United States Patent
Hulme et al.

(10) Patent No.: US 10,501,787 B2
(45) Date of Patent: Dec. 10, 2019

(54) PCR VALIDATION TUBES

(71) Applicant: Starna Scientific Limited, Hainault, Essex (GB)

(72) Inventors: Keith Hulme, Hainault (GB); Nathan Hulme, Hainault (GB); John Hammond, Hainault (GB)

(73) Assignee: Starna Scientific Limited (GB)

( * ) Notice: Subject to any disclaimer, the term of this patent is extended or adjusted under 35 U.S.C. 154(b) by 0 days.

(21) Appl. No.: 14/563,921

(22) Filed: Dec. 8, 2014

(65) Prior Publication Data
US 2015/0160132 A1 Jun. 11, 2015

(30) Foreign Application Priority Data
Dec. 6, 2013 (GB) .................................. 1321609.8

(51) Int. Cl.
*C12Q 1/686* (2018.01)
*G01N 21/64* (2006.01)

(52) U.S. Cl.
CPC ........... *C12Q 1/686* (2013.01); *G01N 21/643* (2013.01); *Y10T 436/10* (2015.01)

(58) Field of Classification Search
None
See application file for complete search history.

(56) References Cited

U.S. PATENT DOCUMENTS

| 2006/0233668 A1 | 10/2006 | Resch-Genger et al. |
| 2008/0038835 A1* | 2/2008 | Westphal ............ G01N 21/278 436/172 |
| 2008/0178653 A1 | 7/2008 | Gunstream |
| 2008/0182263 A1 | 7/2008 | Gunstream |
| 2008/0182264 A1 | 7/2008 | Gunstream |
| 2008/0209978 A1 | 9/2008 | Gunstream |
| 2010/0198525 A1 | 8/2010 | Gunstream |
| 2011/0076687 A1 | 3/2011 | Haberstroh et al. |
| 2011/0231132 A1 | 9/2011 | Gunstream |

(Continued)

FOREIGN PATENT DOCUMENTS

| GB | 2 215 838 A | 9/1989 |
| WO | 00/17627 A1 | 3/2000 |

(Continued)

OTHER PUBLICATIONS

Gudnason, H. et al. Comparison of multiple DNA dyes for real-time PCR: effects of dye concentration and sequence composition on DNA amplification and melting temperature, 2007, Nucleic Acids Research, vol. 35(19) pp. e127 1-e127 8.*

(Continued)

*Primary Examiner* — Xiaoyun R Xu
(74) *Attorney, Agent, or Firm* — Stites & Harbison, PLLC; David W. Nagle, Jr.; James R. Hayne

(57) ABSTRACT

This invention relates to a PCR fluorescence reference standard and to a method for manufacturing a PCR fluorescence reference standard. The PCR fluorescence reference standard comprises a fluorophore suspended in a thermoplastic polymer matrix. The PCR fluorescence reference standard of the invention has a greater shelf life than fluorophores dissolved in a solution and can advantageously be used to validate a fluorescence signal obtained in a thermal cycler.

14 Claims, 1 Drawing Sheet

(56) References Cited

U.S. PATENT DOCUMENTS

| | | | |
|---|---|---|---|
| 2012/0256102 A1* | 10/2012 | Kim | C08G 73/14 250/459.1 |
| 2013/0041595 A1 | 2/2013 | Gunstream | |
| 2013/0115611 A1 | 5/2013 | Gunstream | |
| 2015/0368702 A1 | 12/2015 | Gunstream | |
| 2016/0040222 A1 | 2/2016 | Gunstream | |

FOREIGN PATENT DOCUMENTS

| | | |
|---|---|---|
| WO | 01/35074 A1 | 5/2001 |
| WO | 01/35079 A1 | 5/2001 |
| WO | 2009/108207 A1 | 9/2009 |

OTHER PUBLICATIONS

European Patent Office, Extended European Search Report issued in corresponding Application No. 14004134.4, dated Apr. 15, 2015.

UK Intellectual Property Office, Search Report issued in corresponding Application No. GB1421819.2, dated Sep. 1, 2015.

West, M.A., et al., "Practical Standards for UV Absorption and Fluorescence Spectrophotometry, Developments in Photophysical Instrumentation Part 3," American Laboratory, International Scientific Communications, Inc., US, vol. 9, No. 3, Mar. 1, 1977.

Derose, P.C. "NIST Workshop on Luminescence Standards for Chemical Analysis, Gaithersburg, MD, Sep. 8-9, 1999," Journal of Research of the National Institute of Standards and Technology, vol. 105, No. 4, Jul.-Aug. 2000, p. 631.

Sukumaran, V.S., et al., "Characteristics of dye-doped polymer rods," Dept. of Physics, Anna University, Chennai, India, Nov. 27, 2014, http://een.iust.ac.ir/profs/Sadr/Papers/pmrp5.pdf (downloaded Mar. 3, 2017).

UK Intellectual Property Office, Search Report issued in corresponding Application No. GB1321609.8, dated Jun. 11, 2014.

* cited by examiner

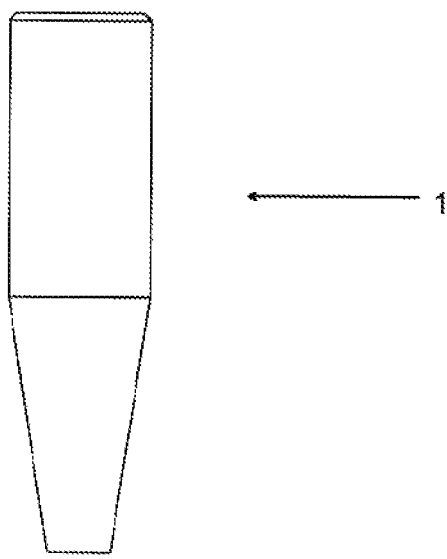

PCR VALIDATION TUBES

FIELD OF THE INVENTION

The present invention relates to means for validating a polymerase chain reaction (PCR) apparatus, also known as thermal cycler. In addition, the present invention relates to a method for validating thermal cyclers.

BACKGROUND OF THE INVENTION

Polymerase chain reaction, hereinafter PCR, is a method of amplifying a DNA target sequence, i.e. a method of producing a large number of copies of a given sequence of DNA, in a relatively short period of time. A PCR reaction solution therefore includes a DNA template having the target sequence, a heat-resistant DNA polymerase, typically Taq or Pfu, a pair of primers, i.e. a pair of short, single-stranded sequences complimentary to the 3' end of the target sequence, and nucleotides to form the sequence copies.

Once the solution is mixed in a PCR tube, the tube is placed in a thermal cycler and exposed to a series of temperature cycles which enable the target sequence to be denatured, each primer to anneal (i.e. bind) to the relevant strand of the target sequence and the nucleotides to bind the primers to form a new strand of DNA complementary to the denatured target sequence in the 5' to 3' direction. The thermal cycles described above are repeated a number of times, usually up to 30.

As PCR allows the production of a large number of copies of target sequences in hours, it is widely used in cloning, genetic engineering, sequencing, functional analysis of genes, molecular detection and diagnosis of hereditary or infectious diseases and identification of genetic fingerprints.

PCR cycles can be subdivided into an exponential phase during which each thermal cycle duplicates the number of target sequences and a plateau phase during which inhibitors of the polymerase reaction found in the amplified sample, nucleotide limitation, accumulation of pyrophosphate molecules, and self-annealing of the accumulating product results in amplification of the target sequence ceasing to occur. If the reaction is halted during the exponential phase, the quantity of starting target sequence can be determined. This is useful, for example in forensic applications in which it is necessary to determine the quantity of starting material. However, if the reaction is carried out until it reaches the plateau phase, it is not possible to quantify the amount of starting material. Accordingly, a newer method based on PCR and called real time PCR or quantitative real time polymerase chain reaction (qPCR) was developed to enable simultaneous amplification, detection and quantification of the target sequence.

Real time PCR is largely similar to traditional PCR in terms of reagents with the addition of intercalating non-specific double-stranded DNA binding fluorescent dyes, fluorescently labeled nucleotides or phosphorus-32 labeled nucleotides. Accordingly, a qPCR thermal cycler combines a thermal system with an optical system capable of detecting fluorescence or radiation and, in addition, software to control the apparatus, collect and analyse data.

Regardless of whether standard PCR or qPCR is used, fluorescence spectroscopy is used in combination with PCR techniques in order to detect specific sequences or to quantify the amount of DNA present in a sample. In fluorescence spectroscopy, there are two aspects that require validation. Firstly, the instrument itself is validated (fluorescence intensity and spectral correction) by comparison to a Certified Reference Material (CRM), also known as Standard Reference Material (SRM). Secondly, analyte detection measurements are also validated by reference to a SRM. As most analyte detection is carried out in a solution, validation of analyte detection measurements is usually performed by comparing the measurement to a solution containing a fluorescent dye.

Metrology is a science which is concerned with measurement; specifically, it includes experimental and theoretical determinations in any field of technology. The international vocabulary of metrology is maintained by the International Organisation for Standardisation (ISO) and is currently in its third revision (VIM 3).

One of the most important concepts in metrology is metrological traceability, which is defined in the ISO/IEC Guide 99:2007 (International vocabulary of metrology—Basic and general concepts and associated terms (VIM)) as the "property of a measurement result whereby the result can be related to a reference through a documented unbroken chain of calibrations, each contributing to the measurement uncertainty." In other words, traceability is the property of the result of a measurement whereby it can be related to references, usually national or international standards, through an unbroken chain of comparisons all having stated uncertainties.

In many countries, national standards for weights and measures are maintained by National Metrology Institutes (NMIs) which provide the highest level of standards for the calibration or measurement traceability infrastructure in that country. For example, in the UK, one NMI is the National Physical Laboratory (NPL); in the US, the NMI is called National Institute of Standards and Technology (NIST); in Germany, one NMI is the Physikalisch-Technische Bundesanstalt (PTB); and, in Canada, the NMI is the NRC Institute for National Measurement Standards (NRC).

Typically, traceability is achieved by calibration which establishes the relation between the result shown in a measuring instrument and the value of a measured standard. Thus, calibration to a traceable standard can be used to determine whether an instrument is precise and accurate and it can also be used to determine whether the instrument has a bias.

There is currently no standard method used to validate thermal cyclers having means for measuring fluorescence of a sample; this is highly undesirable because it means that fluorescence measurements obtained in thermal cyclers are not traceable. Further, use of thermal cyclers in regulated environments has increased dramatically in recent times, accordingly, the requirement to qualify these systems has also increased.

The present invention seeks to provide means for validating a thermal cycler. Further, the present invention aims to provide a method for validating a thermal cycler.

SUMMARY OF THE INVENTION

According to a first aspect of the present invention, a fluorophore suspended in a thermoplastic polymer matrix, which fluorophore suspended in a thermoplastic polymer matrix has fluorescence characteristics within a predetermined uncertainty budget, wherein the polymer matrix is selected from the group consisting of: poly methyl methacrylate (PMMA), polycarbonate (PC); poly oxymethylene (POM); chlorinated polyvinyl chloride (CPVC); and PVC/Acrylic copolymer, is used to validate a thermal cycler.

Advantageously, the polymer matrix comprises poly methyl methacrylate, hereinafter PMMA. The advantage of using PMMA is that it possesses good optical properties and it does not have absorbance peaks.

Preferably, the fluorophore is chosen from the group consisting of: aromatic hydrocarbons and derivatives thereof; bis-benzimides and derivatives thereof; coumarin and derivatives thereof; cyanine and derivatives thereof; fluorescent drugs and derivatives thereof; fluorescent proteins and derivatives thereof; naphtalimide dyes; perylene; xanthene and derivatives thereof; 4',6-diamidino-2-phenylindole; oxazole yellow, derivatives thereof and homodimers thereof; thiazole orange, derivatives and homodimers thereof; pyrenyloxytrisulfonic acid; propidium iodide; ethidium bromide; acridine orange; nitrobenzo-2-oxa-1,3-diazole; tetraphenylbutadiene; oxonol fluorescent dyes; 7-Aminoactinomycin D; aminonaphthalimide dyes; and quinolinium 6-(dimethylamino)-2-[4-[4-(dimethylamino)phenyl]-1,3-butadienyl]-1-ethyl perchlorate.

In a further preferred embodiment, the fluorophore is a conjugate or combination of two or more certified reference materials.

In another preferred embodiment, the fluorophore concentration is below $10^{-2}$ mol/L.

According to a second aspect of the present invention, there is provided a method for manufacturing a PCR fluorescence reference standard comprising the steps of:
(a) providing thermoplastic monomers for making a thermoplastic polymer matrix selected from the group consisting of: poly methyl methacrylate (PMMA), polycarbonate (PC), poly oxymethylene (POM), chlorinated polyvinyl chloride (CPVC), and PVC/Acrylic copolymer;
(b) mixing the thermoplastics monomers with a fluorophore;
(c) carrying out a bulk polymerisation reaction to obtain a thermoplastic polymer matrix comprising a fluorophore suspended substantially uniformly therein;
(d) drying the polymer comprising the suspended fluorophore;
(e) machining the dried polymer comprising the suspended fluorophore; and
(f) polishing the dried polymer comprising the suspended fluorophore.

According to a third aspect of the present invention, there is provided a method of validating a thermal cycler comprising the steps of:
(a) providing a fluorophore suspended in a thermoplastic polymer matrix selected from the group consisting of: poly methyl methacrylate (PMMA), polycarbonate (PC), poly oxymethylene (POM), chlorinated polyvinyl chloride (CPVC), and PVC/Acrylic copolymer;
(b) placing the fluorophore suspended in a thermoplastic polymer matrix of step
(a) in a thermal cycler having means to measure fluorescence; and
(c) validating a fluorescence measurement obtained in the thermal cycler of step (b) by using the fluorophore suspended in a thermoplastic polymer matrix of step (a).

BRIEF DESCRIPTION OF THE DRAWINGS

The present invention will now be described, by way of example only, with reference to the accompanying drawing, in which:
FIG. 1 is a side view of a polymer comprising a fluorophore suspended in a substantially uniform manner, which polymer comprising a suspended fluorophore is suitable for use as a thermal cycler reference standard.

DETAILED DESCRIPTION OF THE INVENTION

FIG. 1 shows a reference standard 1 for use in a thermal cycler. The reference standard 1 is made by following the steps of:
(a) providing suitable thermoplastic monomers;
(b) mixing the thermoplastics monomers with a suitable fluorophore;
(c) carrying out a bulk polymerisation reaction to obtain a polymer comprising a fluorophore suspended substantially uniformly therein;
(d) drying the polymer comprising the suspended fluorophore;
(e) machining the dried polymer comprising the suspended fluorophore; and
(f) polishing the dried polymer comprising the suspended fluorophore.

In other words, the reference standard is produced by mixing a fluorophore or fluorescent dye with, for example, methyl methacrylate monomers and then polymerising the methyl methacrylate monomers using an initiator in a bulk polymerisation process using a suitable initiator, such as, for example, azo compounds or organic peroxides. The resultant material, which will be described herein as a polymer comprising a suspended fluorophore, can then be cut, machined and polished to an optical standard. In the reference standard 1 shown in FIG. 1, the material has been cut to the shape of a PCR tube for use in a thermal cycler. It has surprisingly been found that the addition of a dye at a concentration below $10^{-2}$ mol/L, that is below 0.01 molar, does not adversely affect the polymerisation reaction and, in addition, that the fluorescent properties of the dye are not adversely affected by the polymerisation reaction or the optical properties of PMMA.

A reference standard made as described above provides a means for validating fluorescence measurements obtained in a thermal cycler so that these can be carried out more efficiently and also in such a manner as to make the measurements traceable in a metrology sense. The reference standard obtained from the method described above is advantageous because it has fluorescence characteristics which are within a predetermined uncertainty budget. Accordingly, when the reference standard is used to validate measurements obtained in a thermal cycler comprising means to determine fluorescence of a sample, the measurements are traceable. Thus, the present invention improves traceability of fluorescence measurements obtained in a thermal cycler by allowing the instrument to be calibrated.

Although users would prefer to use a solution containing a fluorescent dye to validate fluorescence intensity and spectral correction in a fluorimeter or other instrument capable of measuring fluorescence, soluble dyes photodegrade quickly, do not have long shelf lives in solution, have environment-dependent fluorescence, and are expensive to produce at high purity. Accordingly, soluble fluorescent dyes are unsuitable for validation of fluorescence intensity and spectral correction.

In contrast, the fluorophore described above is suspended within a solid polymer matrix; thus, the reference standard has a long shelf life and is homogeneous, stable, environmentally independent, highly pure and easy to use. By selecting an appropriate fluorophore from the list below, the fluorescence is detectable within the 260/280 nm end of the spectrum.

Fluorophores widely used in the 260/280 end of the spectrum include:

Aromatic hydrocarbons and their derivatives, for example: anthracene and derivatives thereof, such as dioxoanthracene (DRAQ5—®), naphthalene, ovalene and p-terphenyl.

Bis-benzimides or its derivatives, for example: Hoechst 33342, Hoechst 33258, Hoechst 34580 (also known as Hoechst dyes).

Coumarin and its derivatives, for example: hydroxycoumarin, aminocoumarin, methoxycoumarin.

Cyanine and its derivatives, for example: Cy2, Cy3, Cy3B, Cy5, Cy5.5, Cy7, TruRed 490, SYTOX Green.

Fluorescent drugs such as: mepacrine (also known as quinacrine), quinine, mithramycin, chromomycin A3, and olivomycin;

Fluorescent proteins such as: R-Phycoerythrin (PE), Peridinin-chlorophyll-protein (PerCP), allophycocyanin (APC), phycocyanin, phytocoerythrin, phycoerythrocyanin, green fluorescent protein (GFP).

Naphtalimide dyes.

Polycyclic aromatic hydrocarbons such as perylene.

Xanthene and its derivatives, including: rhodamine and derivatives thereof, such as: carboxy-X-rhodamine (ROX), sulforhodamine acid chloride (Texas Red—®), tetramethylrhodamineisothiocyanate (TRITC), tetramethyl rhodamine (TAMRA); fluorescein (FAM) and derivatives thereof, such as, hexachlorofluorescein (HEX), tetrachlorofluorescein (TET), NED dyes, 5'-dichloro-dimethoxy-fluorescein (JOE—®).

Other fluorescent dyes include: 4',6-diamidino-2-phenylindole (DAPI); oxazole yellow (YO), its derivatives and homodimers, for example: YOYO-1; thiazole orange (TO) its derivatives and homodimers, for example: TOTO-1, TOTO-3; pyrenyloxytrisulfonic acid (Cascade Blue—®); propidium iodide (PI); ethidium bromide; acridine orange; nitrobenzo-2-oxa-1,3-diazole (NBD); tetraphenylbutadiene; oxonol fluorescent dyes, for example, fluorescent red 610; 7-Aminoactinomycin D (7-AAD) LDS 751; aminonaphthalimide dyes, such as, Lucifer yellow (®); and quinolinium 6-(dimethylamino)-2-[4-[4-(dimethylamino)phenyl]-1,3-butadienyl]-1-ethyl perchlorate (sold as LDS 751).

Moreover, conjugates or combinations of two or more of the fluorophores mentioned above are also widely available. Examples of conjugates of two or more fluorophores are: Red 613 (PE-Texas Red); PE-Cy5 conjugates; PE-Cy7 conjugates; TruRed (PerCP-Cy5.5 conjugate)' APC-Cy7 conjugates; TO-PRO-1; and TO-PRO-3.

Exemplary fluorophores suitable for use in a reference standard wherein a fluorophore is suspended in a thermoplastic polymer matrix include: anthracene, napthalene, ovalene, p-Terphenyl, tetraphenylbutadiene, compound 610, and rhodamine.

These fluorophores are available at sufficiently high purity for use as a reference material without the need for further purification. Any of the above fluorophores can be suspended in a thermoplastic polymer to form a solid, homogeneous material capable of being machined into a size suitable for a thermal cycler.

Once the reference material of the invention has been machined into the form of a PCR tube, the thermal cycler can be validated.

In order to be used as a reference standard, a material must be tested for degradation over time. Testing for degradation includes ascertaining stability of the material in the short-term (during measurement), mid-term (repeat measurements) and long-term (recalibration period, lifetime). The fluorophores suspended in a polymer matrix according to the present invention were tested for short-term, mid-term and long-term degradation.

Short- and mid-term degradation testing of the PCR fluorescence reference standards of the present invention involved analysing repeatability and reproducibility of measurements obtained using the reference standards.

As a results of the tests it was established that the reference standards of the present invention are simple to use because the fluorophores used are suspended in a solid matrix polymer matrix and therefore the standards do not involve sample preparation. Further, the suspended fluorophores do not evaporate, are robust and easy to use and store.

Moreover, the suspended fluorophores absorb and emit in the same region as test materials compared to measurements of a biological assay in the same conditions, i.e. the reference standards of the present invention have suitable absorption and emission properties.

Additionally, fluorescence quantum yield of the PCR fluorescence reference standards of the present invention was independent of excitation wavelength. Also, the suspended fluorophores of the present invention provide minimum absorption and emission overlap and have a small temperature dependence. In summary, degradation tests concluded that the PCR fluorescence reference standards of the present invention are not degradable in the short-term or mid-term.

To investigate the long-term stability PCR fluorescence reference standards according to the invention were exposed to optical radiation with the aim of accelerating degradation under damaging conditions. The spectral irradiance of these optical sources was measured using an array spectroradiometer calibrated against an NMI spectral irradiance standard lamp between 200 nm and 1000 nm. The measured optical sources included, amongst others, a UV curing lamp (single high pressure mercury linear fluorescence lamp of the type widely used in industry for curing UV adhesives and paints) and a UV sterilisation lamp (single low pressure mercury linear fluorescence lamp such as Philips TUV G15 T8, typically used for germicidal applications due to the high UV-C emission at 254 nm). Although other light sources were also used, the UV curing lamp and the UV sterilisation lamps were the most aggressive light sources; thus, description of the results will be limited to these light sources. Tables 1 and 2 below show the observed spectral irradiance of UV curing lamp and UV sterilisation lamp respectively.

TABLE 1

| Spectral irradiance (W $m^{-2}nm^{-1}$) Curing lamp | Wavelength (nm) |
|---|---|
| 0 | 200 |
| 0 | 300 |
| 1 | 400 |
| 0.4 | 500 |
| 1.6 | 600 |
| 0.1 | 700 |
| 0.1 | 800 |
| 0.1 | 900 |
| 0.1 | 1000 |

TABLE 2

| Spectral irradiance (W m$^{-2}$nm$^{-1}$) UV sterilisation lamp | Wavelength (nm) |
|---|---|
| 0 | 200 |
| 0 | 300 |
| 0.4 | 400 |
| 1.1 | 450 |
| 0 | 500 |
| 0 | 600 |
| 0 | 700 |
| 0 | 800 |
| 0 | 900 |
| 0 | 1000 |

Total irradiance was calculated as the integrated sum of the spectral irradiance over all wavelengths. Normalising against the highest irradiance, the relative irradiance of each individual source was calculated. The normalised irradiance (log. Scale) of the UV curing lamp was 1.000 and the normalised irradiance (log. Scale) of the UV sterilisation lamp was 0.04. This value provides an indication of the relative risks of photo bleaching with exposure over time. Using the calculated total irradiance values, long-term stability can be estimated. The PCR fluorescence reference standards show no change after exposure to the UV curing lamp over 30 minutes, which is equivalent to exposure under room lighting condition for 3.5 days, and exposure in the a standard spectrofluorometer equivalent to 70 days. If different UV ratios produced by different light sources are taken into account, the exposure length for the PCR fluorescence reference standards under normal illumination is increased. If the reference standards are exposed only to the excitation from a standard spectrofluorometer for less than 30 minutes per day, the optical irradiation tests described above predict that the PCR fluorescence reference standards will be stable for approximately 10 years.

Accordingly, the incorporation of fluorophores in PMMA matrix gives a much greater shelf life, estimated to be around 10 years.

Although the invention has been specifically described as using methyl methacrylate monomers, it would also be possible to use certain other monomers to form a solid polymer matrix, such as polycarbonate (PC) and polyoxymethylene (POM), chlorinated polyvinyl chloride (CPVC) and PVC/Acrylic copolymer. The requirements of any thermoplastic used are: transparency, homogeneity and robustness.

PMMA is a transparent thermoplastic material often used as an alternative to glass in analytical laboratories around the world because it is highly transparent, homogeneous and does not have absorbance peaks.

The invention claimed is:

1. A method of validating a thermal cycler comprising the steps of:
   (a) providing a fluorophore suspended in a thermoplastic polymer matrix selected from the group consisting of: poly methyl methacrylate (PMMA), polycarbonate (PC), poly oxymethylene (POM), chlorinated polyvinyl chloride (CPVC) or PVC/Acrylic copolymer, the fluorophore characterized by a metrologically valid procedure for one or more specified properties, accompanied by a certificate that provides for each of the one or more specified properties, the value of the specified property, its associated uncertainty, and a statement of metrological traceability, and the thermoplastic polymer matrix is cut to the shape of a PCR tube;
   (b) placing the fluorophore suspended in a thermoplastic polymer matrix of step (a) in a thermal cycler having means to measure fluorescence; and
   (c) validating a fluorescence measurement obtained in the thermal cycler of step (b) by using the fluorophore suspended in a thermoplastic polymer matrix of step (a);
      wherein validating the fluorescence measurement obtained in the thermal cycler includes confirming by examination and the provision of objective evidence that the fluorescence measurement obtained in the thermal cycler matches the one or more specified properties of the fluorophore within the associated uncertainty.

2. The method of validating a thermal cycler as recited in claim 1, wherein the fluorophore is homogenously suspend in the thermoplastic polymer matrix.

3. A method of validating a thermal cycler, comprising the steps of:
   suspending a fluorophore in a thermoplastic polymer matrix, wherein the fluorophore has fluorescence characteristics within a predetermined uncertainty budget, and wherein the polymer matrix is selected from the group consisting of: poly methyl methacrylate (PMMA), polycarbonate (PC), poly oxymethylene (POM), chlorinated polyvinyl chloride (CPVC) or PVC/Acrylic copolymer, and the thermoplastic polymer matrix is cut to the shape of a PCR tube; and
   validating the thermal cycler using measurements obtained in the thermal cycler and the predetermined uncertainty budget of the fluorophore;
   wherein validating the thermal cycler includes confirming by examination and the provision of objective evidence that the measurements obtained in the thermal cycler match the fluorescence characteristics of the fluorophore within the predetermined uncertainty budget.

4. The method of validating a thermal cycler as recited in claim 3, wherein the thermoplastic polymer matrix is a PMMA matrix.

5. The method of validating a thermal cycler as recited in claim 3, wherein the fluorophore is a certified reference material chosen from the group comprising: coumarin and derivatives thereof, xanthene and derivatives thereof, cyanine and derivatives thereof, aromatic hydrocarbons and derivatives thereof, fluorescent proteins and derivatives thereof, bis-benzimides and derivatives thereof, fluorescent drugs and derivatives thereof, 4',6-diamidino-2-phenylindole, oxazole yellow, derivatives thereof and homodimers thereof, thiazole orange, derivatives and homodimers thereof, pyrenyloxytrisulfonic acid, propidium iodide, ethidium bromide; acridine orange; nitrobenzo-2-oxa-1,3-diazole, tetraphenylbutadiene, oxonol fluorescent dyes, 7-Aminoactinomycin D, aminonaphthalimide dyes, quinolinium 6-(dimethylamino)-2-[4-[4-(dimethylamino)phenyl]-1,3-butadienyl]-1-ethyl perchlorate;
   wherein the certified reference material is characterized by a metrologically valid procedure for one or more specified properties, accompanied by a certificate that provides for each of the one or more specified properties, the value of the specified property, its associated uncertainty, and a statement of metrological traceability.

6. The method of validating a thermal cycler as recited in claim 5, wherein the fluorophore is a conjugate or combination of two or more certified reference materials.

7. The method of validating a thermal cycler as recited in claim 3, wherein the fluorophore concentration is below $10^{-2}$ mol/L.

8. The method of validating a thermal cycler as recited in claim 3, wherein the fluorophore is characterized by a metrologically valid procedure for one or more specified properties, accompanied by a certificate that provides for each of the one or more specified properties, the value of the specified property, its associated uncertainty, and a statement of metrological traceability.

9. A method of operating a thermal cycler comprising the steps of:
(a) providing a reference standard cut to the shape of a PCR tube, the reference standard including a fluorophore suspended in a thermoplastic polymer matrix selected from the group consisting of: poly methyl methacrylate (PMMA), polycarbonate (PC), poly oxymethylene (POM), chlorinated polyvinyl chloride (CPVC) or PVC/Acrylic copolymer, the reference standard having predetermined values of fluorescent intensity and spectral correction within a predetermined uncertainty budget;
(b) placing the reference standard of step (a) in a thermal cycler having means to measure fluorescence; and
(c) validating a fluorescence measurement obtained in the thermal cycler of step (b) by comparing a measured fluorescent intensity and spectral correction of the reference standard of step (a) to the predetermined values of fluorescent intensity and spectral correction for the reference standard.

10. The method of operating a thermal cycler as recited in claim 9, wherein, if the measured fluorescent intensity and spectral correction obtained in the thermal cycler do not match the predetermined values of fluorescent intensity and spectral correction within the predetermined uncertainty budget, further comprising a step of calibrating the thermal cycler.

11. The method of operating a thermal cycler as recited in claim 9, wherein the fluorophore is homogenously suspend in the thermoplastic polymer matrix.

12. The method of operating a thermal cycler as recited in claim 9, wherein the reference standard is homogenous and stable.

13. The method of operating a thermal cycler as recited in claim 9, wherein the reference standard shows no change after exposure to a UV curing lamp over 30 minutes.

14. The method of operating a thermal cycler as recited in claim 9, wherein the reference standard is stable for approximately 10 years.

\* \* \* \* \*